US006884438B1

(12) United States Patent
Quintanar et al.

(10) Patent No.: US 6,884,438 B1
(45) Date of Patent: Apr. 26, 2005

(54) METHOD FOR PREPARING VESICULAR NANOCAPSULES

(75) Inventors: David Quintanar, Colinas de Lago,C.Izc. (MX); Hatem Fessi, Lyons (FR); Eric Doelker, Conches; Eric Allemann, Croix-de-Rozon, both of (CH)

(73) Assignee: Universite Claude Bernard Lyon I, Villeurbanne Cedex (FR)

( * ) Notice: Subject to any disclaimer, the term of this patent is extended or adjusted under 35 U.S.C. 154(b) by 0 days.

(21) Appl. No.: 09/462,492

(22) PCT Filed: Jul. 21, 1998

(86) PCT No.: PCT/FR98/01611

§ 371 (c)(1),
(2), (4) Date: Mar. 9, 2000

(87) PCT Pub. No.: WO99/04766

PCT Pub. Date: Feb. 4, 1999

(30) Foreign Application Priority Data

Jul. 24, 1997 (FR) .............................. 97 09672

(51) Int. Cl.[7] ............................ A61K 9/16; B01J 13/02; B32B 15/02

(52) U.S. Cl. ..................... 424/490; 524/801; 524/803; 524/804; 524/845; 428/402.21; 428/402.22; 264/4.1; 424/489; 424/496; 424/499

(58) Field of Search ................................ 524/801, 803, 524/804, 845; 428/402.21, 402.22; 264/4.1; 424/489, 490, 496, 499

(56) References Cited

U.S. PATENT DOCUMENTS

| 4,329,332 | A | * | 5/1982 | Couvreur et al. .............. 424/9 |
| 4,968,350 | A | * | 11/1990 | Bindschaedler et al. .... 106/170 |
| 5,500,224 | A | * | 3/1996 | Vrancky et al. ............ 424/451 |

* cited by examiner

Primary Examiner—Samuel A. Acquah
(74) Attorney, Agent, or Firm—Dennison, Scheiner, Schultz & Wakeman

(57) ABSTRACT

A process for the preparation of nanoparticles for the encapsulation of active constituents, the nanocapsules prepared being dispersible in aqueous phase in colloidal form, non-toxic, biocompatible, stable in colloidal suspension and economical. In the process, two non-oily solvents as used, together with a third, oily solvent.

13 Claims, 1 Drawing Sheet

US 6,884,438 B1

METHOD FOR PREPARING VESICULAR NANOCAPSULES

FIELD OF THE INVENTION

The technical field of the invention is that of nanoparticles, in particular, for the encapsulation of active constituents of medical, cosmetic, dietetic, fertiliser or other nature. They are therefore, in other words, colloidal systems carrying in particular active constituents. Such colloidal systems preserve these active constituents and can allow their controlled and/or extended release at the level of their site of action. These systems can also have the vocation of masking the taste and/or of reducing the toxicity of certain active constituents.

More precisely, this invention concerns the preparation of nanocapsules likely to include at least one active constituent, these nanocapsules being vesicles whose envelope consists of at least one macromolecular material.

This invention also concerns the nanocapcules as obtained by this procedure, the colloidal suspensions comprising these nanocapsules, and the compositions, for example therapeutic, comprising such nanocapsules whether in colloidal suspension or not.

DESCRIPTION OF RELATED ART

There are three families of submicroscopic vectors allowing the transport of active constituents, namely:

Liposomes, nanospheres and nanocapsules.

Liposomes are submicronic particles whose wall consists of one or more leaves, each comprising a phospholipid-base bilayer. Liposomes have in particular the following disadvantages:
a) Physical instability
b) Chemical instability of the constituent phospholipids (e.g. hydrolyses or formation of peroxides
c) Bad reproducibility from batch to batch
d) Loss of the active constituent Nanospheres represent matrix type structures consisting of solid spheres, in which the active constituent is trapped and/or dissolved.

Nanocapsules are vesicles comprising an envelope which is generally of macromolecular nature. The active constituent(s) is/are likely to be contained in the core limited by the said envelope and adsorbed on the envelope of the vesicles.

There is extensive literature on the characterisation and the preparation of these nanoparticular colloidal vectors carrying active constituents.

As an illustration of the nanospheres family, one can mention U.S. Pat. No. 5,118,528, which describes matrix type polymer-based nanoparticles obtained according to a technique in which:

on one hand one dissolves a filmogenous material consisting of a polymer of lactic acid in acetone (phase I) and on the other hand one prepares a larger volume of a second liquid phase (phase II) consisting mainly of a non-solvent of the filmogenous material, this non solvent being e.g. water.

The tensioactives can be added to phase I containing the polymer and/or the aqueous phase II. They consist for example of a glycol polypropylene and of a non ionic tensioactive added in the aqueous phase II. According to this procedure, phases I and II are placed in presence under magnetic agitation of 100 rpm. The mixture formed is opalescent, which evidences the formation of nanoparticles or spherical vesicles of lactic acid polymers of a diameter roughly equivalent to 200 nanometers. The acetone is eliminated from this colloidal suspension of nanoparticles by drawing under vacuum. The water can also be eliminated by ultrafiltration and drying, to produce a powder of nanospheres. In addition to or instead of the water in phase II, an alcohol such as ethanol can be used. These matrix type nanospheres do not give full satisfaction, in particular with regard to the following points:

a) low yield
b) need for large volumes of solvent
c) difficulty to control the size of the particles It is also possible to prepare matrix type nanospheres by using a technique of extraction of the solvent of the polymer constituting said nanospheres. This technique is based on the restoration of the miscibility of the polymer solvent, in the solvent forming the homogenous continuous phase of the colloidal suspension. This is the salting out technique. It is described in particular in U.S. Pat. No. 4,968,350. The procedure described in this patent consists in preparing a first concentrated aqueous solution of a solid of the electrolyte type (e.g. MgCl2) to which is added a sufficient quantity of a protective colloid (e.g. polyvinylic alcohol) so as to produce a viscous solution or a gel. A second solution is also prepared, based on a non water-soluble polymer and forming the material making up the nanospheres. This polymer is for example cellulose acetate or cellulose acetophtalate. The solvent employed is acetone. Then one mixes the two solutions I and II with each other under agitation, so as to obtain an emulsion of the polymer solution II in the aqueous gel of polyvinylic alcohol+MgCl2. The nanospheres are obtained as a result of the extraction of the acetone from the polymer heterogeneous phase to the continuous aqueous phase II. This transfer is obtained by adding water to the emulsion, which causes the restoration of physiochemical conditions permitting the acetone and the water to be miscible. The MgCl2 concentration is reduced to below a limit concentration. According to a variant, no agent of the MgCl2 type is used, making the acetone insoluble in the polymer solution II. In this case, the latter is directly emulsified in the hydrocolloid. The organic salts and solvents can be eliminated by tangential flow filtration in order to recover the nanocapsules in the form of an aqueous colloidal dispersion in the form of powder by centrifugation/drying of the dispersion.

The nanospheres obtained by salting out naturally suffer from the disadvantages attached to this type of nanoparticles carrying active constituents. These include:

a) use of large quantities of acetone and salts
b) long purification stages
c) possible incompatibility between the salt and certain bioactive compounds
d) large quantities of residual polyvinylic alcohol, which is not acceptable for an intravenous administration.

Nanocapsules have the advantage over nanospheres and liposomes in that they permit a better protection of the active constituents incorporated or encapsulated, and similarly a better control of their release in vivo. They also permit the incorporation of large quantities of oily active constituents.

Among the traditional techniques of preparation of nanocapsules, interfacial polymerisation occupies a good position. This technique is a polymerisation of monomers to the interface of an oil-in-water or water-in-oil emulsion. The polymer develops forming a wall around heterogeneous phase globules, which finally leads to an envelope encapsulating said heterogeneous phase containing or not containing the active constituent. This thus produces a multitude of vesicles in suspension in the continuous phase.

Traditionally nanocapsule envelope polymers are acrylic, methacrylic or alkyl cyano(meth)acrylic polymers. U.S. Pat. No. 4,329,332 reveals the preparation of nanocapsules by the introduction of the alkylcyanoacrylate monomer in an aqueous solution of a tensioactive agent preferably non ionic, such as polyhydroxethyl-sorbitan monolaurate. The medium is then subjected to a vigorous agitation so as to form a micellar solution. This solution's pH is adjusted to 2–3 using a physiologically acceptable acid. The addition of any active constituent is effected by dissolution in the reactional aqueous phase. The nanocapsules obtained have a size of roughly 200 nanometers. Additionally, it should be noted that the acid pH of the aqueous phase can be damaging to a certain number of active constituents. The nanocapsules according to this patent also have the disadvantage of involving monomers which are potentially toxic in residual state. These nanocapsules also have the disadvantage that a chemical reaction is possible between the polymer and certain active constituents.

Patent application PCT WO 94/15 590 describes nanocapsules whose envelope polymer consists of an alkyl-2-cyanopolyacrylate (alkyl=4-ter-octyl-phenyl, 2'-carboxethyl-, hexadecyl-,). According to this procedure, one uses absorbent alkylcyanoacrylate monomers (ester of cyanoalcrylic acid with glycol polyethylene) or lipophile monomers (hexadecyl-2-cyanoacrylate) and one uses mono- or biphase systems. In the monophase systems, the active constituent itself consists of the dispersed phase acting as a support for the polymerisation which leads to the nanocapsules. In the biphase systems involving two liquids not miscible with each other, the active constituent is contained in one of the phases, the whole forming the dispersed phase of the emulsion, seat of the interfacial polymerisation.

Application PCT WO 94 17789 reveals more precisely nanocapsules obtained by interfacial polymerisation, in a biphase system.

U.S. Pat. No. 5,500,224 reveals a pharmaceutical composition comprising colloidal suspensions of nanocapsules prepared by interfacial polymerisation of n-butyle-2-cyanoacrylate on micellae comprising pH 4.3 acetic acid buffer and a tensioactive of the type sodium laurylsulphate. The continuous oily phase consists of mygliol (fatty acid triglyceride in C8–C10) with added sorbitanne monoleate (SPAN 80).

The nanocapsules obtained have a diameter of roughly 250 nanometers. The active constituent is contained in the dispersed aqueous phase forming the core of the nanocapsules.

Interfacial polymerisation can also be used to prepare nanospheres.

The nanoparticles obtained by interfacial polymerisation present a number of disadvantages, some of which are mentioned hereunder.

In certain cases, this technique involves organic solvents which are pharmaceutically redhibitory due to their high toxicity. It is then essential to purify the nanocapsules by eliminating these undesirable solvents. This substantially complicates the procedure and heavily increases its cost.

This technique can also involve the use of macromolecules of the serum albumine or dextran types the major difficulty with which is that they are immunogenic.

Additionally, the alkylcyanoacrylates are envelope polymers whose biocompatibility still leaves much to be desired. Also, the toxicity of the monomers used to prepare these polymers is certain, and that of the products obtained after biodegradation.

Besides, the technique of interfacial polymerisation is relatively constrictive therefore expensive in particular with regard to the polymerisation conditions.

To be complete, we will also point out the existence of FR 2 084 199, which concerns the obtaining not of nanocapsules but of microcapsules, by the salting out technique. Thus, this patent deals with the preparation of spherical microgranulateds flowing freely, solid, and comprising a polymer matrix coating liquid or solid particles of encapsulated substances. This procedure comprises the following stages:

a-preparation of a solution of the encapsulating polymer (ethylcellulose) in a solvent (n-butanol) at the most 15% soluble in weight in water at 20 deg.C.;

b-dissolution or dispersion in solution a, of a solid or liquid coating material, for example paraffin oil;

c-dispersion of the solution or emulsion obtained (organic phase A) in an aqueous liquid (aqueous phase R=water saturated with n-butanol) not miscible with the organic solvent;

d-slow migration under the control of the organic solvent (n-butanol) of the organic phase A in the aqueous phase B, so that the dissolved polymer is deposited on the surface of the particles dispersed in B, this migration acting by incorporation of water in the medium;

e-separation and possibly drying of the solidified particles, i.e. the mixture of granulated particles.

The vesicles obtained are microcapsules having a diameter of between 80 and 500 u. These vesicles consist of a core base of paraffin oil enveloped with ethyl cellulose. It is clear that the solvent n-butanol is used in this procedure in pure form and not in the form or a solution of water in the n-butanol. Besides, this procedure is constrictive in that it forces a solvent to be selected whose solubility in water does not exceed 15% in weight at 20 deg.C.

SUMMARY OF THE INVENTION

In this state of the technique, one of the main objectives of this invention is to supply a procedure for the preparation of nanocapsules loaded or not loaded with active constituents and formed of vesicles whose envelope consists of at least one polymer, the said nanocapsules having to be:

dispersible in liquid phase, for example aqueous, in colloidal form, exempt from toxic products, formed of biocompatible and possibly biodegradable substances, stable in colloidal suspension, able to protect the active constituent which might be encapsulated, and similarly to allow a prolonged and/or controlled release of the active constituent in vivo, obtainable simply and economically.

Another main objective of this invention is to supply a procedure for preparing nanocapsules of the type of that mentioned above and which is also easy and profitable to use on an industrial scale.

Another objective of the invention is to supply a procedure for preparing nanocapsules of the type of that mentioned above making it possible to obtain reliably and in a reproducible manner particles of a size of under 1 um.

Another main objective of this invention is to supply a procedure for preparing nanocapsules of the type of that mentioned above and not requiring heavy and costly purification stages.

Another main objective of this invention is to supply a procedure for the preparation of nanocapsules of the type of that mentioned above and permitting the encapsulation of a large variety of active constituents of absorbent or lipophile type.

Another objective of the invention is to supply a colloidal composition of nanocapsules obtained according to the procedure mentioned above and meeting the expected specifications, in particular in the pharmaceutical field, for oral, parenteral dermic administration or for applications on mucous membranes.

Another objective of the invention is to supply a therapeutic composition comprising nanocapsules or the above-mentioned colloidal suspension.

Having set itself all these objectives, the applicant has had the merit to reveal, both surprisingly and unexpectedly, that it is possible to prepare nanocapsules involving two non-oily phases, not miscible with one another and a third oily phase;

by carrying out an oil-in-water emulsion, whose oily dispersed phase contains the envelope polymer;

and by extracting the solvent from the envelope polymer contained in the lipophile dispersed phase by effecting such that the conditions of the continuous phase are such that the envelope polymer solvent again becomes partly miscible in the continuous phase.

Thanks to these measures, the applicant has been able to observe with astonishment, after extensive work and tests, that the solidification of the polymer occurred at the interface of the emulsion and developed by forming the walls of the nanocapsules enclosing the heterogeneous phase.

It follows that the objectives set initially, among others, have been attained by this invention, which concerns a procedure for the preparation of nanocapsules (NC) likely to comprise at least one active constituent (AC), these nanocapsules being vesicles of average size under 1000 um and whose envelope consists of at least one polymer (PE), characterised in that it consists mainly;

1-of using at least three liquid substances (S1, S2, S3), at least one envelope polymer, and possibly one or more active constituents (AC), these substances being selected in such a way that:

S1 is an organic solvent/dispersant, at least partly miscible with S2 and S3, and acting as a solvent and/or dispersant of PE and of the possible AC, S2 is a non-solvent of PE, not miscible with S3, S3 is a liquid, preferably an oily phase, not solvent of PE and solvent/dispersant of the possible AC; S3 being also intended to enter the constitution of the core of the NCs, 2-of achieving a first homogeneous liquid phase I comprising a solution of PE, of S3 and possible of AC in S1; S1 being brought through a solution of S2, in S1, preferably saturated with S2;

3-of preparing a second homogeneous liquid phase II, comprising the solvent S2 and in which S1 can be emulsified, 4-of placing in presence phases I and II, adding to them possibly at least one stabilising tensioactive substance, 5-of effecting the placing in emulsion of the mixture obtained in stage 4, to produce an emulsion of I in II, 6-of adding some solvent S2 in the emulsion I/II, so as to set in the homogeneous phase II conditions such that S1 is at least partly miscible with S2, and thus to permit the diffusion of S1 in phase I in phase II, to obtain at the end the NC in suspension in another continuous phase III, 7-possibly, of eliminating all or part of S1 and/or S2.

The procedure according to the invention is hinged around the choice of the solvent/dispersant S1 and of the non-solvent S2, and of the partial miscibility of S1 and of S2.

Another basis of the invention concerns the achievement of an emulsion whose dispersed phase contains the envelope polymer, the solvent/dispersant S1, the possible AC and the oil S1, and whose continuous phase mainly contains S2, the conditions being such that S1 is no longer soluble in S2.

The procedure of the invention is also based on the measure according to which one ends the non miscibility of S1 in S2, after completing the emulsion, so as to draw S1 from the dispersed phase towards the continuous phase and thus to allow the solidification of the envelope polymer and subsequently the formation of the nanocapsules. There only remains to eliminate S1 and all or part of S2.

Lastly, the preferred characteristic of mutual saturation of the solvents S1, S2 in stage 2, benefits, against all expectations, the obtaining of the nanoparticles of an average size of less than one micron.

BRIEF DESCRIPTION OF THE DRAWINGS

The sole drawing FIGURE is a photomicrograph of nanocapsules according to the invention.

DETAILED DESCRIPTION OF THE INVENTION

Figure 1:
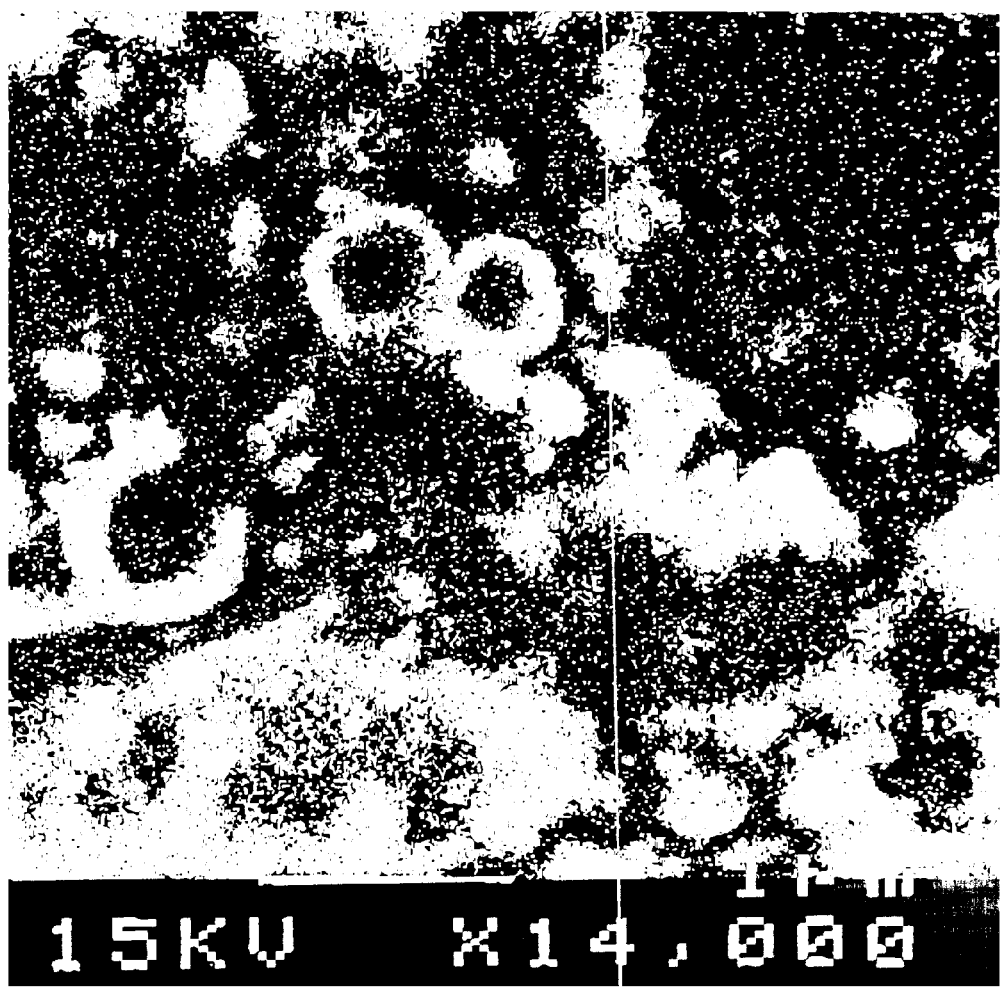

Such a procedure is convenient to be carried out. It leads to nanocapsules of an average size of less than 1000 nanometers, preferably 500 nanometers. The stability in colloidal suspension of these nanocapsules is proven. It confers on the active constituent that they are likely to encapsulate either in their core, or by adsorption on their wall, a protection in storage and in their transport to the action site. These nanoparticles are in fact perfectly appropriate to be used as a colloidal system for the vectorisation of active constituents, in particular of the pharmaceutical type. These nanocapsules are not toxic both at the end product stage and at the methodological stage through the materials and devices used to obtain them.

The fact of using an oil, an emulsion of the oil-in-water type and a solidification of the polymer shell by a solvent extraction based on the creating of conditions of solubilisation or miscibility in the non-oily continuous phase, are completely innovative elements which reflect the merit and the inventive nature of the procedure considered in this description.

The inventive activity is further reinforced by the fact that it was absolutely not predictable that the polymer would solidify at the interface according to a parietal structure. The solidification could for instance have occurred in the mass of the heterogeneous, preferably oily phase.

The notions of solubility and miscibility referred to, as a non limitative example, within this description are explained in particular in chapter 14 page 340 and following of the work PHARMACOPEE GMP.

We will return in detail hereunder to stage (1) of the procedure according to the invention consisting in the choice of the raw materials S1, S2, S3, PE and possibly AC.

In stage (2), a first homogeneous liquid phase I is prepared by dissolving envelope polymer PE and liquid S, preferably oily, and possibly active constituent AC in solvent S1.

In accordance with the invention, the latter can be used pure or consist of a solution of non-solvent S2 in S1.

In such a case, it is preferable (without it being limitative) that this solution of S2 is S1 be saturated in S2. This makes easier stage (3)—the emulsification of phase I in phase II—since it does without the latency time induced by the saturation of S2 in S1. The mutual saturation of the solvents enhances the emulsification process.

In practice, this stage (2) is achieved conventionally, in containers, preferably fitted with agitation equipment. This stage is carried out advantageously at ambient temperature and at atmospheric pressure.

Stage (3) of the procedure according to the invention is that during which the second homogeneous liquid phase II is prepared. This phase II is characterised in that it comprises the solvent S2 and in that it constitutes a medium in which S1 and more generally phase I can be emulsified.

According to a variant 3' of this stage (3), a phase II is prepared comprising solely S2 or consisting of a solution of S1 in S2, S1 not being at saturation point. In such a case one does so that in stage (5) the quantities of phase I and II (Total volumes in S1 and S2) used in proportion such that the emulsion of I is formed in II. In this variant 3', it is therefore important first of all that phase I mixed with phase II brings S1 to saturation in S2, before the emulsion I/II occurs. This extends stage (3) in such a way as in the case mentioned above, that phase I is not formed by a non-saturated solution of S2 in S1.

In a variant 3" of stage (3), a phase II is prepared based on S2 and comprising:

a-either S1 at saturation point b-or at least an agent A able to make S1 not miscible with S2 c-nor a combination of a and b.

In this variant, sub-variants a, b, and c have the vocation to improve the formation of the emulsion and, in the best case, to enable the emulsion to occur instantly after the mixing of phases I and II.

In any case according to invention, preference is given to the procedure according to which, when phases I and II are mixed, solvent S1 and non-solvent S2 are only partly miscible in one another.

In practice, one preferably uses, in phase I a solution of S1 saturated with S2, and in phase II a solution of S2 saturated with S1.

Stage (3) occurs ideally with the same equipment and in the same conditions of temperature as in stage (2). The same applies to stages (4) and (5) involving the placing in presence and emulsification of phases I and II.

According to an advantageous provision of the invention, the emulsioning (5) is carried out under vigorous agitation, preferably using mechanical means operating at a rate of 1500 rpm, preferably 5,000 rpm, and more preferentially still included between 7,000 and 10,000 rpm.

As an example of an emulsification device suitable for the procedure according to the invention, one can mention a mechanical agitator with a screw or a homogeniser (ultra-Turrax®).

The formation of the nanocapsules NC by solidification of the polymer PE at the interface of emulsion I in II, occurs at stage (6). In this stage, S1 must be made to be miscible with S2.

In a preferred way, this is achieved by completing emulsion I/II using solvent S2.

According to a variant which can be envisaged in the event that one uses in phase II an agent able to make S1 not miscible in S2, it is possible to plan the formation of NC by dilution of the external phase using water and to eliminate A by an appropriate means (e.g. by tangential-flow filtration).

Once the transfer of S1 in the homogeneous phase II has been completed, one carries out in stage (7) the elimination of all or part of S1 and/or S2. Advantageously, S1 is eliminated by any appropriate means such as drawing by more or less substantial vacuum, evaporation, distillation or any other fractionating method.

After elimination of S1 from phase II, one obtains a colloidal suspension of nanocapsules NC in S2. This suspension can be more or less concentrated by elimination and/or addition of S2.

The other methods used to eliminate S2 can be the same as those used to eliminate S1. In practive, one can for instance purify the suspension by tangential-flow filtration, so as to collect the nanocapsules NC which can then be dried, so as to produce them in dry and solid form. It is also perfectly envisageable to carry out an atomisation or a lyophilisation (whether or not in the presence of a cryoprotective agent) of the nanocapsules NC in suspension.

These nanocapsules NC are perfectly characterised and have a stable and well defined structure. Once formed, they impart on the suspension a milky white aspect with bluish reflections which is perfectly revelatory and specific.

These nanocapsules also have specific densities and sedimentation speeds, which help differentiate them from the other nanoparticles such as the nanospheres included in nanoemulsions.

The stability of the colloidal suspension according to the invention is at least one year.

Advantageously, the temperature of application of the procedure is included between 4 and 45 deg.C., preferably between 15 and 25 deg.C.

According to a preferred provision of the invention, the proportions of S1, S2, S3 and PE are selected such that the size of the NCs is less than 1000 nn, these proportions being, preferably, as follows (expressed in % in relation to S1):

PE included 0.1 and 100, preferably between 0.5 and 20 dry weight/volume,

S2 included between 51 and 1000, preferably between 100 and 500 V/V

S3 included between 0.1 and 10, preferably between 0.1 and 5.0 V/V.

In any case, it should be arranged so that, quantitatively, the proportion of S2 is as small as possible so as to have a concentrated suspension of nanocapsules. The same applies to the quantities of S1 used, so as to ease the elimination of the latter.

The nanocapsules NC produced by this procedure according to the invention have advantageously a controlled size of less than 1000 nanometers, preferably less than 500 nanometers, and more preferentially included between 50 and 350 nanometers.

Concerning the products used in the procedure in accordance with the invention, we state hereunder, without it being limitative, the groups of substances S1, S2, PE and AC, which we would preferably choose.

The solvent S1 is advantageously selected in the family of the alcohols, phenols, ketones, esters of carboxylic acids and their mixtures.

More precisely, the following product groups are retained for S1:

Ethyl acetate, benzylic alcohol, propylene carbonate, butanol, butanone and their mixtures.

The non-solvent S2 is advantageously a liquid or a mixture of liquids containing water and/or at least one alcohol. Thus S2 is selected more specially from the following group of products:

Water, alcohol—for instance ethanol, propylene-glycol or glycerine—and their mixtures.

Liquid S3, preferably, oily is selected from the family of vegetable or mineral oils, neutral oils, essential oils, fatty acids, esters of carboxylic acids, terpenes, vitamins and their mixtures.

Advantageously, the following oily products will be retained:

Mygliol®810, 812 and 840 (Dynamit Nobel, Germany), Labrafac® lipophilique, Lauroglycol (Gattefosse, France), mineral oil, olive oil, sesame oil, corn oil, cotton oil, groundnut oil, benzyl benzoate, isoprpyl myristate, essential oil of lavender, essential oil of bouquet, vitamin E, clofibrate, etc.

With regard to the envelope polymers PE, the selections is made from the bicompatible natural and synthetic homo- and/or copolymers. These can be for example polylactic acid D or L and DL, copolymers of lactic acid and glycolic acid; poly e-caprolactone; polypropiolactone; polybutylrolactone; polypivalactone; cellulose butyrate acetate; ethylcellulose; hydroxymethylpropylcellulose phtalate; lacquer gum; polyvinyl aceto-phtale; cellulose acetophtalate; the acrylates and the acrylic polymers (Eudragit®, Rohm Pharma, Germany); the polymers obtained from cyclic esters of the hydroxybutyric, hydroxyisobutyric, hydroxymethylvaleric, phenyl-lactic, hydroxyethylbutyric acids, benzyl polybetamalate, the alkyl polycyanoacrylates, the polyethylene-vinyl acetate; and their mixtures.

In accordance with the invention, the PE is selected from the following polymer groups:

- (co)polymer of a-hydrocarboxylic acid(s), preferably lactic acid and/or glycolic acid, (co)polymer of (meth) acrylic acid and/or of methacrylate,
- poly-e-caprolactone,
- cellulose and its derivatives,
- polymer block of a-hydroxycarboxylic acid and of ethylene polyoxyde,
- cyanoacrylates,
- and copolymers and/or mixtures between them.

The active constituents AC likely to be encapsulated in the nanocapsules NC prepared in accordance with the invention, may be diverse and varied. The condition to be observed as to the choice of the active constituent resides in its solubility and/or in its aptitude to dispersion in the solvent S1. Generally speaking, these can for example be active constituents used in allergy treatment, in anaesthesia, in cancerology, cardiology and angiology, dermatology, endocrinology, gastroenterology, gynaecology, haematology, hepatology, immunology, infectrology, neurology, ophtamology, parasitology, pneumology, rheumatology, stomatology, toxicology, or used as antalgics or anti-inflammatories, etc.

Preferably, the active constituent is chosen from the following product groups:

Indometacine, hormones—preferably progecterone-Estradiol-,Chlorambucil, S3, vitamins (preferably vit. E and K), cyclosporine A, ibuprofen, propanolol, valproic acid, clofibrate, etc. and their mixtures.

Concerning the stabilising tensioactives suitable for stage (4) of the procedure according to the invention, one should choose preferably in accordance with the invention from among the ionic or non-ionic tensioactives. More precisely, one can choose for example the polyvinylic alcohols for instance Mowiol® 4-88 (Hocchst, Frankfurt, Germany); the poloxamers for example Pluronics® F-68 and F-127 (BASF, Wyandotte, USA); the biliary salts for example sodium glycocolate and the carboxylic acid salts such as sodium oleate.

The advantages of the procedure are numerous, and include:

- reliability
- high yield
- reproducibility
- easy scale transposition for industrial applications
- use of unsophisticated conventional equipment (in particular high-pressure homogenisers or ultrasonication devices are not essential)
- use of non toxic solvents, stabilisers and additives well tolerated by the body
- control of the size of the nanocapsules NC obtained.

According to another of these aspects, this invention also aims at nanocapsules NC per se such as those obtained by the procedure defined above or by any other procedure leading to the same result or to a similar result.

In particular, the invention has as its object nanocapsules NC smaller than 1000 nanometers, preferably smaller than 500 nanometers, the wall of which consists of at least one polymer PE such as described above and which comprises, whether at trace state or not, substances S1 and/or S2 and/or S3, and possibly an active constituent AC; these substances being as defined above.

This invention also concerns a colloidal suspension of nanocapsules NC characterised in that it is obtained from the product leaving stage (6) of the procedure as defined above and/or by redispersing the nanocapsules NC obtained at the end of stage (7) of the said procedure, in a non-solvent of PE.

Another object of the invention consists of a therapeutic composition comprising the NCs loaded with AC and obtained by the procedure as presented above or by a procedure leading to the same product.

This invention will be better understood in the light of the examples given below. The latter will also highlight all the advantages and the variants of implementation of the procedure according to the invention. Additionally, these examples will include the characterisation and the evaluation of the properties of the nanocapsules NC in accordance with this invention.

To complete the illustration given by the examples, we provide as an appendix a single FIG. 1 representing a photograph taken with an electronic scan microscope of the nanocapsules according to the invention—magnification: ×14,000.

EXAMPLES

Example 1

Preparation of Nanocapsules of Biodegradable Polymer Containing an Organic Liquid On one hand, 200 mg of polymer PE of lactic acid D,L (MEDISORB®100 DL) AND 0.5 ml of triglycerides of caprilyc/capric acids—oil S3—(Mygliol®812)are dissolved in 20 ml of ethyl acetate S1 saturated with water=S2 (Phase I).

On the other hand, 2 g of polyvinytic alcohol (Mowiol® 4-88), a tensioactive agent, are dissolved in 40 ml of purified water (S2) saturated with ethyl acetate S1 (Phase II). Phase I based on S1 saturated with S2 (ethyl acetate+water), is emulsioned in the aqueous phase II (S2) under vigorous agitation (about 800 rpm) for ten minutes. 200 ml of water=S2 are added to the emulsion under agitation in order to allow the diffusion of the ethyl acetate towards the aqueous phase II. The mixture (phase III) becomes milky white with bluish reflections due to the formation of the nanocapsules NC whose wall consists of PE.

The ethyl acetate S1 is eliminated under reduced pressure (water pump vacuum) and the suspension is concentrated, by elimination of the water S2, under the same conditions, to the desired volume.

The size of the nanocapsules NC measured in a laser ray diffractometer (Nanosizer® from the firm Coultronics) is 329 nm with a dispersion index of 2.

The existence of the nanocapsules NC has been confirmed, on one hand, by cryofracture of the nanocapsules and observation by electronic scan microscope (FIG. 1) and, on the other hand, by the comparison of the sedimentation speed under ultracentrifugation of the nanocapsules according to the invention and of nanoemulsions or pilot nanospheres prepared by the same method with this difference that for the nanoemulsions, there is no polymer PE in the preparation and for the nanospheres, there is no oil S3 in the preparation. Thus, the sedimentation speed of nanoemulsions, nanospheres and nanocapsules differs due to the different constitutions and consequently to their density. The density of these systems can be measured by isopyenic centrifugation (on a density gradient of colloidal silica (Percoll®, Pharmacia, LKB, Sweden). The centrifugation was effected at 4 deg.C. and 1500 g for 3 hours. Marker tubes of known densities (Sephadex®, Pharmacia) were used to calculate the density of the systems. After centrifugation, it is measured by the distance (h) between the dispersion meniscus and the band containing the nanoparticles.

Results

Nanoemulsions: There is no sedimentation (h=0)

Considering that the density of Mygliol® 812 is 0.9438 g/cm3 (calculated with a pyenometer) it is logical that the oil contained in the nanoemulsion tends to float.

Nanospheres: Sedimentation (h=55.12 mm).

Density calculated=1.405 g/cm3

The high sedimentation shows the solid matrix constitution of the particles.

Nanocapsules: Sedimentation (h=14.98 mm)

Density calculated—1.0357 g/cm3

This sedimentation indicates an intermediate state between a nanoemulsion and nanospheres.

This indicates that the polymer and the oil are part of the particles.

The fact that there is only one band confirms the vesicular structure in which the oil forms the core.

Example 2

Preparation of Nanocapsules Containing Cosmetic Oils

The procedure is as given in example 1 but the Mygliol® 812 is replaced by a mineral oil in phase I of ethyl acetate/water.

The nanocapsules NC have a size of 303 nm with a dispersion index of 2.

Example 3

Preparation of Nanocapsules Containing an Essence

The procedure is as given in example 1, but the Mygliol® 812 is replaced by 0.1 ml of essential oil of lavender at the level of the ethyl acetate phase I. The nanocapsules NC have a size of 304 nm with a dispersion index of 2.

Example 4

Preparation of Nanocapsules Containing a Lipophile Dye

The procedure is as given in example 1, but 5 mg of Soudan III are added to the ethyl acetate phase I.

The nanocapsules have a size of 340 nm with a dispersion index of 2.

The suspension of the nanocapsules is then centrifugated at 20,000 rpm for 40 minutes. The deposit is dried under vacuum in a dessicator. Approximately 30 mg of the dry product are dissolved in 50 mg of chloroform. The absorbance of the solution is measured at 518 nm in reference to a calibration curve. The percentage of Soudan III encapsulated (related to the percentage of the initial content) is 100.8%.

Example 5

Preparation of Nanocapsules with a Solubility Polymer Dependent on the pH

The procedure is as given in example 1, but replacing the polymer PE and the solvent S1 respectively by Eudragit®E (soluble acrylic polymer with gastric pH) and by carbonate propylene.

The nanocapsules NC have a size of 239 mn with a dispersion index of 3.

Example 6

Preparation of Nanocapsules with a Solubility Polymer Dependent on the pH, Containing a Lipophile Dye The procedure is as given in example 4, but the polymer PE and the solvent S1 respectively are replaced by Eudragit®E and by benzylic alcohol.

The nanocapsules have a size of 287 nm with a dispersion index of 2.

The percentage of Soudan III encapsulated after tangential filtration (Minitan® device) is 92.4%.

Example 7

Preparation of Nanocapsules Containing a Solid Active Constituent

The procedure is as given in example 1, but 20 mg of indometacine are added to the phase I of ethyl acetate S1 saturated with water S2.

The nanocapsules have a size of 314 nm with a dispersion index of 2.

The suspension is centrifugated and dried as in example 1. Approximately 30 mg of the dry product are dissolved in 20 mg of chloroform. After a suitable dilution with chloroform, the absorbance is measured at 248 nm in reference to a calibration curve.

The percentage of indometacine encapsulated is 94.4%.

Example 8

Preparation of Nanocapsules Containing a Liquid Active Constituent

The procedure is as given in example 1, but the oil S3 (mygliol) is replaced by clofibrate S3. The nanocapsules have a size of 317 nm with a dispersion index of 2.

The suspension is centrifugated and dried as in example 4.

Approximately 25 mg of the dry material are dissolved in 20 ml of chloroform.

The absorbance is then measured at 280 nm in reference to a calibration curve.

The percentage of clofibrate encapsulated is 95.3%.

Example 9

Preparation of Nanocapsules Containing a Cosmetic Active Constituent

The procedure is as given in example 1, but the oil is replaced by vitamin E to form S3.

The nanoparticles have a size of 322 nm, with a dispersion index of 2.

The suspension is centrifugated and dried as in example 4.

Approximately 20 mg of the dry product are dissolved in 20 mg of chloroform. The absorbance is then measured at 297 nm, in reference to a calibration curve. The percentage of vitamin E encapsulated is 92.2%.

What is claimed is:

1. Process for the preparation of nanocapsules which are vesicles of an average size of less than 1000 nm and which comprise at least one active constituent within an envelope comprising at least one polymer, comprising the steps of:
   a) obtaining at least three liquids, S1, S2 and S3, wherein S1 is an organic solvent or dispersant at least partially miscible with S2 and S3, and which is a solvent or dispersant for the at least one polymer and the at least one active constituent, S2 is a non-solvent for the at least one polymer and is not miscible with S3, and S3 is a non-solvent for the at least one polymer and a solvent or dispersant of the at least one active constituent;
   b) producing a first homogeneous liquid phase I comprising a solution of S3, the at least one active constituent and the at least one polymer in S1, S1 being brought into phase I by means of a solution of S2 in S1;
   c) preparing a second homogeneous liquid phase II comprising solvent S2 and optionally including S1 emulsified therein;
   d) mixing together liquid phases I and II;
   e) forming an emulsion of liquid phase I in liquid phase II;
   f) adding S2 to the emulsion to form in homogeneous phase II conditions in which S1 is at least partially miscible with S2, and S1 diffuses from phase I to phase II, to obtain thereby the nanocapsules in a new continuous phase III; and
   g) optionally eliminating at least part of S1, S2 or both S1 and S2.

2. A process according to claim 1, wherein S3 is an oily solvent.

3. A process according to claim 1, wherein in step d), at least stabilizing substance is added.

4. A process according to claim 1, wherein in step b), S2 is at saturation in S1.

5. A process according to claim 1, wherein in step c), a phase II is prepared consisting essentially of S2 or a solution of S1 in S2 where S1 is not in saturation.

6. A process according to claim 1, wherein in step c), a phase II is prepared based on S2 comprising 1) S1 at a saturation point, 2) an agent A which renders S1 not miscible with S2, or both 1) and 2).

7. A process according to claim 1, wherein the step e) of forming an emulsion is carried out by mechanical agitation at a speed of about 1500 rpm.

8. A process according to claim 1, wherein the eliminating of at least part of S1, S2 or both S1 and S2 is carried out by evaporation, tangential filtration, centrifugation, ultracentrifugation, or drawing under vacuum.

9. A process according to claim 1, wherein the at least one polymer is present in an amount of 0.1 to 100% dry weight to volume with respect to S1, S2 is present in an amount of 51 to 1000% volume/volume with respect to S1 and S3 is present in an amount of 0.1 to 10% volume/volume with respect to S1.

10. A process according to claim 9, wherein the at least one polymer is present in an amount of 0.5 to 20% dry weight to volume with respect to S1, S2 is present in an amount of 100 to 500% volume/volume with respect to S1 and S3 is present in an amount of 0.1 to 0.5% volume/volume with respect to S1.

11. A process according to claim 1, wherein:
   S1 is selected from the group consisting of ethyl acetate, benzylic alcohol, carbonate propylene, butanol, butanone and mixtures thereof;
   S2 is selected from the group consisting of water, ethanol, propylene glycol, glycerine and mixtures thereof;
   S3 is selected from the group consisting of triglycerides of caprylic/capric acids, triglycerides of medium chain fatty acids, lauroglycol, mineral oil, olive oil, sesame oil, corn oil, cotton oil, groundnut oil, benzyl benzoate, isopropyl myristate, essential oil of lavender, essential oil of bouquet, vitamin E, clofibrate, and mixtures thereof;
   the at least one polymer is selected from the group consisting of lactic acid polymers, glycolic acid polymers, acrylic acid polymers, methacrylic acid polymers, acrylate polymers, methacrylate polymers, poly-e-caprolactone, cellulose, cellulose derivatives, block polymers of α-hydroxycarboxylic acid and ethylene oxide, cyanoacrylates, and copolymers and mixtures thereof; and
   the at least one active component is selected from the group consisting of indometacine, hormones, chlorambucil, S3, a vitamin, cyclosporine A, ibuprofen, propanolol, valproic acid, clofibrate and mixtures thereof.

12. A colloidal suspension of nanocapsules obtained according to the process of claim 1 from step f), or by redispersing the nanocapsules from step g) in a non-solvent for the at least one polymer.

13. A therapeutic composition comprising nanocapsules containing at least one active component obtained according to the process of claim 1.

* * * * *